United States Patent
Amit et al.

(10) Patent No.: US 10,365,230 B1
(45) Date of Patent: Jul. 30, 2019

(54) SCATTEROMETRY OVERLAY BASED ON REFLECTION PEAK LOCATIONS

(71) Applicant: KLA-Tencor Corporation, Milpitas, CA (US)

(72) Inventors: Eran Amit, Haifa (IL); Tzahi Grunzweig, Timrat (IL)

(73) Assignee: KLA-Tencor Corporation, Milpitas, CA (US)

( * ) Notice: Subject to any disclaimer, the term of this patent is extended or adjusted under 35 U.S.C. 154(b) by 476 days.

(21) Appl. No.: 14/661,448

(22) Filed: Mar. 18, 2015

Related U.S. Application Data

(60) Provisional application No. 61/955,317, filed on Mar. 19, 2014.

(51) Int. Cl.
*G01N 21/956* (2006.01)
*G01B 11/27* (2006.01)

(52) U.S. Cl.
CPC ........... *G01N 21/956* (2013.01); *G01B 11/27* (2013.01); *G01N 2201/127* (2013.01)

(58) Field of Classification Search
None
See application file for complete search history.

(56) References Cited

U.S. PATENT DOCUMENTS

| | | | |
|---|---|---|---|
| 7,929,667 B1 * | 4/2011 | Zhuang | H05G 2/005 378/119 |
| 8,189,202 B2 | 5/2012 | Liesener et al. | |
| 8,553,227 B2 | 10/2013 | Jordanoska | |
| 8,792,096 B2 | 7/2014 | Straaijer | |
| 2015/0022822 A1 | 1/2015 | Grunzweig et al. | |

FOREIGN PATENT DOCUMENTS

WO 2014138522 A1 9/2014

OTHER PUBLICATIONS

Mike Adel, Diffraction order control in overlay metrology—a review of the roadmap options, KLA-Tencor Corporation (Israel) Migdal Ha-Emek 23100, Israel, 2008 SPIE Digital Library, 19 pages.*

James C. Wyant, Basic Wavefront Aberration Theory for Optical Metrology, 1992, 64 pages.*

(Continued)

*Primary Examiner* — Tung S Lau
(74) *Attorney, Agent, or Firm* — Suiter Swantz pc llo

(57) ABSTRACT

Metrology methods and modules are provided, which comprise measuring intensity spatial distributions and peaks of spots at the pupil plane of a metrology system that correspond to various diffraction orders scattered from target cells and calculating overlay(s) of the target cell(s) from the measured intensity spatial distributions and peaks. For example, intensity peak or distribution of zeroth diffraction orders from four cells, first diffraction orders from two cells as well as diffraction orders from a single cell may be used to derive an overlay estimation, which may also be compared to standard overlay measurements for different purposes. Intensity spatial distributions may also be used to derive weight function for adjusting measurements or the metrology system.

13 Claims, 7 Drawing Sheets

(56) References Cited

OTHER PUBLICATIONS

Eric K. Lin, Feature-shape and Line-edge Roughness Measurement of Deep sub-micron Lithographic Structures using Small-angle Neutron Scattering, 2001, 10 pages.*

Craig R. Forest, Metrology of thin transparent optics using Shack-Hartmann wavefront sensing, 2004, 12 pages.*

Qiu J., WJ Zhang, LH Liu, Pf Hsu, LJ Liu. "Reflective properties of randomly rough surfaces under large incidence angles," http://www.ncbi.nlm.nih.gov/pubmed/24977364, accessed Feb. 20, 2015.

Adel, Mike, Daniel Kandel, Vladimir Levinski, Joel Seligson and Alex Kuniaysky. "Diffraction order control in overlay metrology—a review of the roadmap options," http://spie.org/Publications/Proceedings/Paper/10.1117/12.773243, Metrology, Inspection, and Process Control for Microlithography XXII, Proc. of SPIE vol. 6922, 692202 (2008).

* cited by examiner

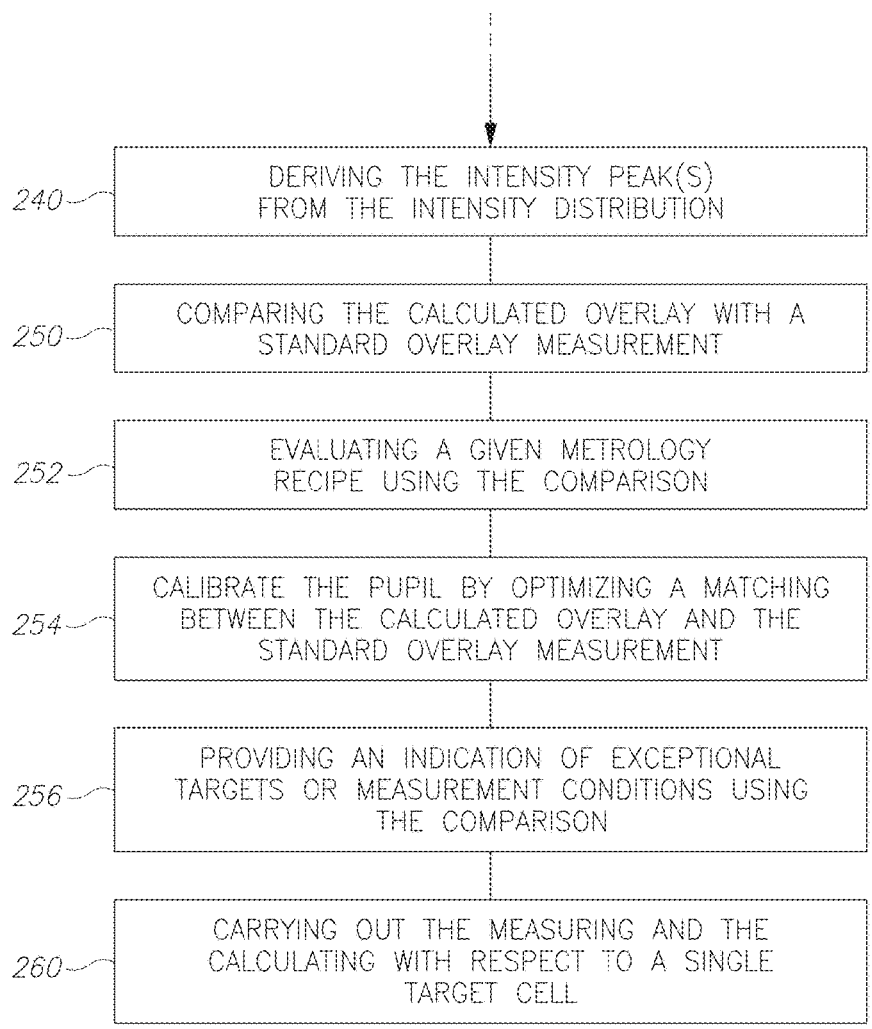
Figure 4 (cont. 1)

SCATTEROMETRY OVERLAY BASED ON REFLECTION PEAK LOCATIONS

CROSS REFERENCE TO RELATED APPLICATIONS

This application claims the benefit of U.S. Provisional Patent Application No. 61/955,317 filed on Mar. 19, 2014, which is incorporated herein by reference in its entirety.

BACKGROUND OF THE INVENTION

The present invention relates to the field of metrology, and more particularly, to overlay metrology.

In angle resolved scatterometry overlay (SCOL) metrology measurements the scattered light from a periodic target is measured using a broad range of illumination angles. The scattered light originating from each illumination angle is measured over multiple cells and\or multiple diffraction orders. These multiple measurements provide the required information for the overlay calculation.

SUMMARY OF THE INVENTION

One aspect of the present invention provides a method comprising measuring an intensity peak of at least one spot at a pupil plane of a metrology system that corresponds to a specified diffraction order scattered from at least one specified target cell; and calculating an overlay of the at least one target cell from the at least one measured intensity peak.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1:
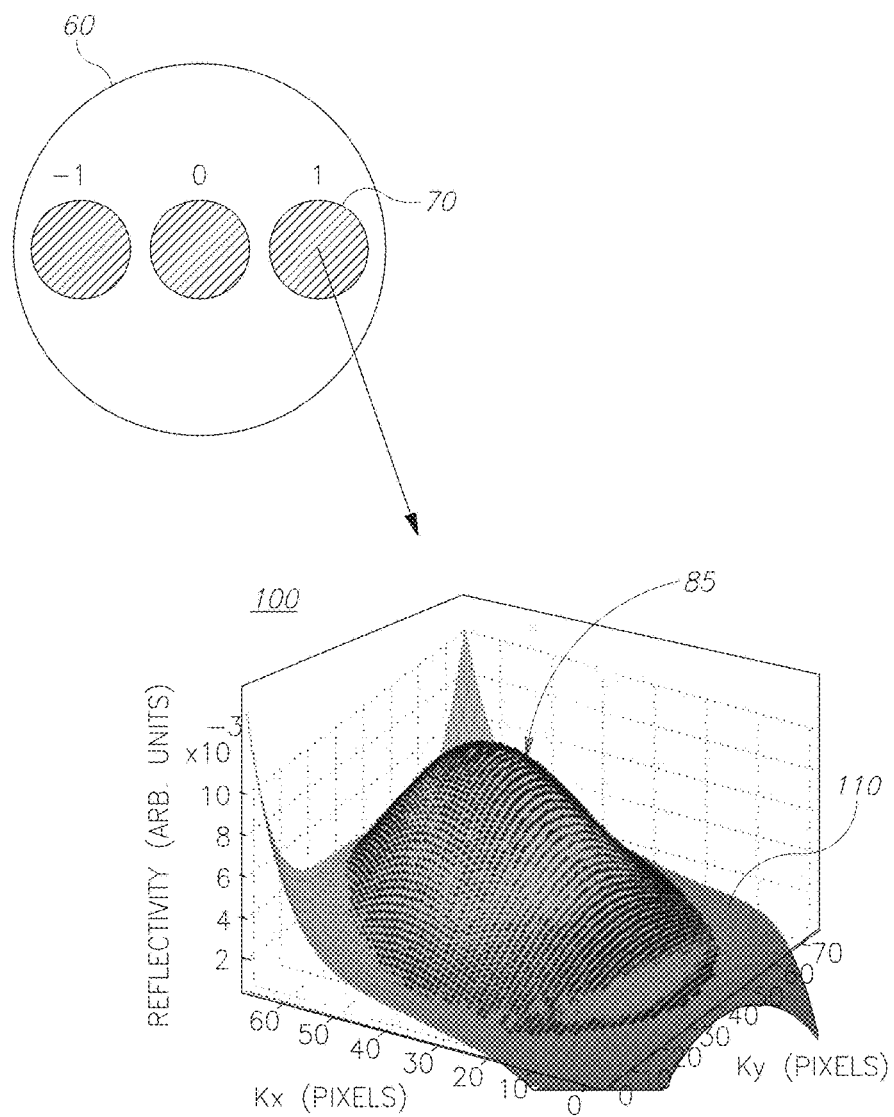
FIG. 1 is a high level schematic illustration of scattered light at a pupil plane in a SCOL measurement, according to some embodiments of the invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Metrology methods and modules are provided, which comprise measuring intensity spatial distributions and peaks of spots at the pupil plane of a metrology system that correspond to various diffraction orders scattered from target cells and calculating overlay(s) of the target cell(s) from the measured intensity spatial distributions and peaks. For example, intensity peak or distribution of zeroth diffraction orders from four cells, first diffraction orders from two cells as well as diffraction orders from a single cell may be used to derive an overlay estimation, which may also be compared to standard overlay measurements for different purposes. Intensity spatial distributions may also be used to derive a weight function for adjusting measurements or the metrology system.

FIG. 1 is a high level schematic illustration of scattered light at a pupil plane 60 in a SCOL measurement, according to some embodiments of the invention. In first order SCOL, two cells containing grating-over-grating targets are measured. Each cell has a different intended OVL (overlay) shift between the layers (usually marked as $+f_0$ and $-f_0$ for the first and the second cell, respectively). The top of FIG. 1 schematically illustrates pupil plane 60 with spots 70 representing the zeroth and the ±1 diffraction orders scattered from one of the target cells and measured by the SCOL metrology tool (the distance between the centers of spots 70 is equal to the illumination wavelength over the target grating pitch). The reflected light in pupil plane 60 for a given target cell and diffraction order may have one peak (or possibly several peaks) because the target reflection coefficients are continuous functions of the scattering angles and the illumination beam's spatial intensity (in the pupil plane) has one or more maxima. The bottom of FIG. 1 illustrates an example for the intensity spatial distribution across spot 70 as represented by data points 85 showing such an intensity peak for a specific spot 70 (illustrated, in a non-limiting manner, is a first order spot 70). Certain embodiments comprise calculating a target overlay based on the peak's location, i.e., based on the maxima location of reflectively per spot (i.e., per target cell and diffraction order). For example, in the illustration a model 100 for the intensity spatial distribution is derived by fitting an approximation function 110 to intensity spatial distribution 85, such as a polynomial approximation function (illustrated is a fifth order polynomial function as a non-limiting example). From the curved surface, the maximum may be calculated and used to refine overlay measurements. In certain embodiments, approximation function 110 representing intensity spatial distribution 85 may be used to calculate weight functions (e.g., respective to pupil points) which may be applied to the overlay measurements and provide information for tool calibrations. Approximation function 110 may be used to improve reflection image qualities such as pupil centering and stretching, dividing by reference image etc.

Model 100 may be applied to different SCOL measurement techniques such as zero order SCOL and first order SCOL. In the former, model 100 may be applied to reflection images from the four target cells, while in the latter, model 100 may be applied to the +1 and −1 diffraction orders from the two target cells. Model 100 may be applied to any number of spots 70.

In certain embodiments, model 100 may be enhanced by image processing techniques to identify a peak location, to select among several peaks or to derive a weight function from the intensity spatial distribution.

In the following, an overlay calculation is exemplified in a non-limiting manner for first order SCOL. Peak locations may be described as function of the cell offset and the diffraction order as K=f(OFFSET, Order). Using linear approximation the peak locations may be expressed as K=a·OFFSET. The four peaks may be represented by the following:

$$K_{1,1}=P \cdot a_1 \cdot (f_0+OVL)$$

$$K_{1,-1}=P \cdot a_{-1} \cdot (f_0+OVL)$$

$$K_{2,1}=P \cdot a_1 \cdot (-f_0+OVL)$$

$$K_{2,-1}=P \cdot a_{-1} \cdot (-f_0+OVL)$$

The first K index indicates the target cell (1 or 2 which corresponds to the intended shift $+f_0$ and $-f_0$ respectively, with OVL representing the unintended overlay) and the second K index indicates the diffraction order (−1 or +1 which corresponds to the linear coefficient $a_1$ and $a_{-1}$ respectively). It is noted that the different coefficients $a_1$, $a_{-1}$ for the +first and −first diffraction orders (respectively) may reflect the optic system imperfections such as differences between the optical paths for the ±first order. The factor P transforms from NA (numerical aperture) coordinates into field coordinates (nm). Summing up the peak locations with respect to one coordinate system (−1 orders being opposite to +1 orders) results in the expression: $K_{1,1}-K_{1,-1}+K_{2,1}-K_{2,-1}=2P[a_1-a_{-1}]OVL$, i.e., the sum of the four peak locations is proportional to the OVL. Furthermore, since the peak movements of the different orders are expected to be roughly similar ($a_1 \approx -a_{-1}$), only one cell peak can be used, e.g., for the first cell: $K_{1,1}-K_{1,-1} \approx 2Pa_1 \cdot (OVL+f_0)$.

Figure 2A:
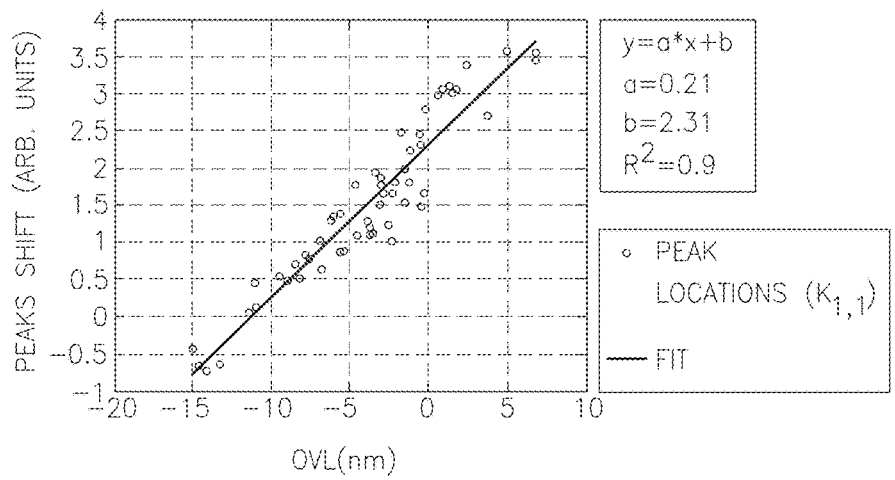
FIGS. 2A-2D provide an experimental verification of the presented model and results, according to some embodiments of the invention.
Figure 2B:
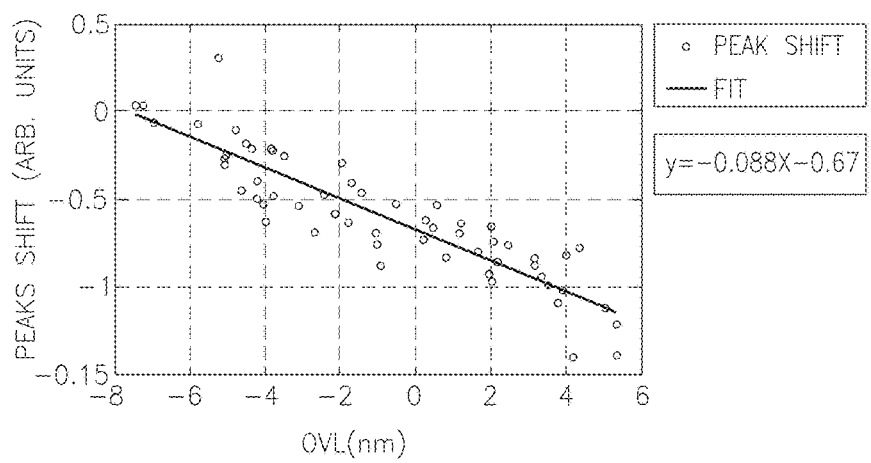
Figure 2C:
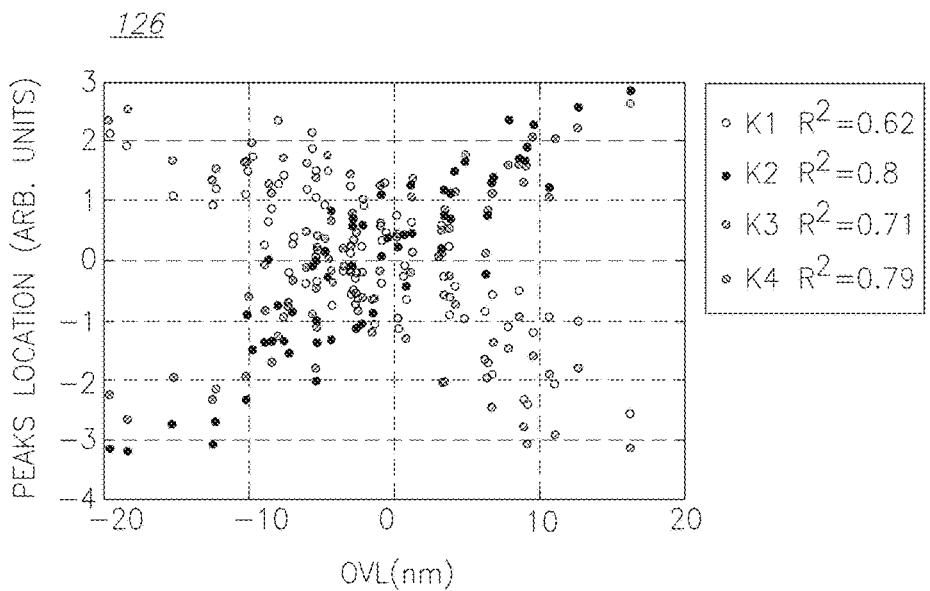

FIGS. 2A-2D provide an experimental verification of the presented model and results, according to some embodiments of the invention. FIG. 2A presents in diagram 122 the first cell first order peak locations $K_{1,1}$, as function of the overlay (OVL), which is shown to be linear. FIG. 2B presents in diagram 124 the measurements from a single cell ($K_{1,1}-K_{1,-1}$, denoted peak shift) as a function of the overlay (OVL), which is likewise shown to be linear (for a different dataset). It is noted that the peak shift for OVL=0 is proportional to the intended shift $-f_0$. FIG. 2C presents in diagram 126 the individual peak movement (peak location minus average location across the wafer, denoted K1=$K_{1,1}$, K2=$K_{1,-1}$, K3=$K_{2,1}$, K4=$K_{2,-1}$) as a function of the standard target OVL (for a different dataset). The data illustrates the correlations between the peak locations and the overlay across the wafer. Hence it is demonstrated that overlays may be correctly estimated using the deviations of peak locations within spots 70.

Furthermore, the overlay OVL may be calculated from the four expression for the peak locations, for example using the formula:

$$OVL = \frac{K_{1,1}-K_{1,-1}+K_{2,1}-K_{2,-1}}{K_{1,1}-K_{1,-1}-K_{2,1}+K_{2,-1}} f_0$$

Figure 2D:
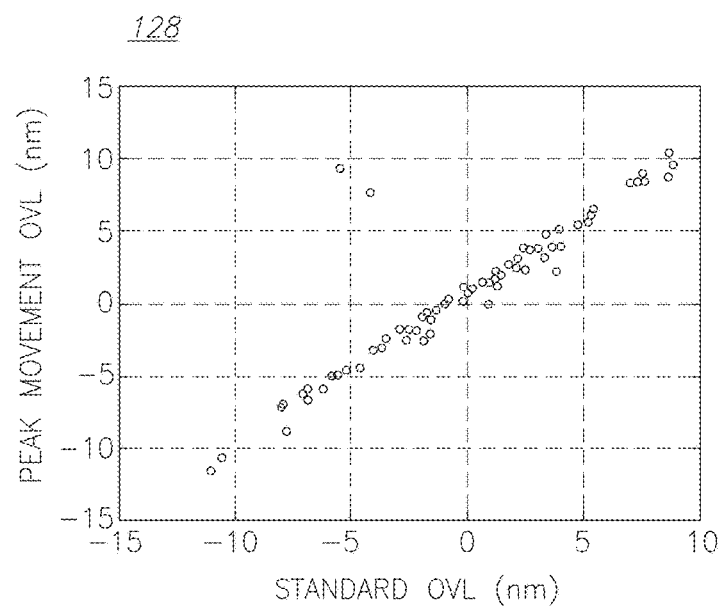
Figure 3A:
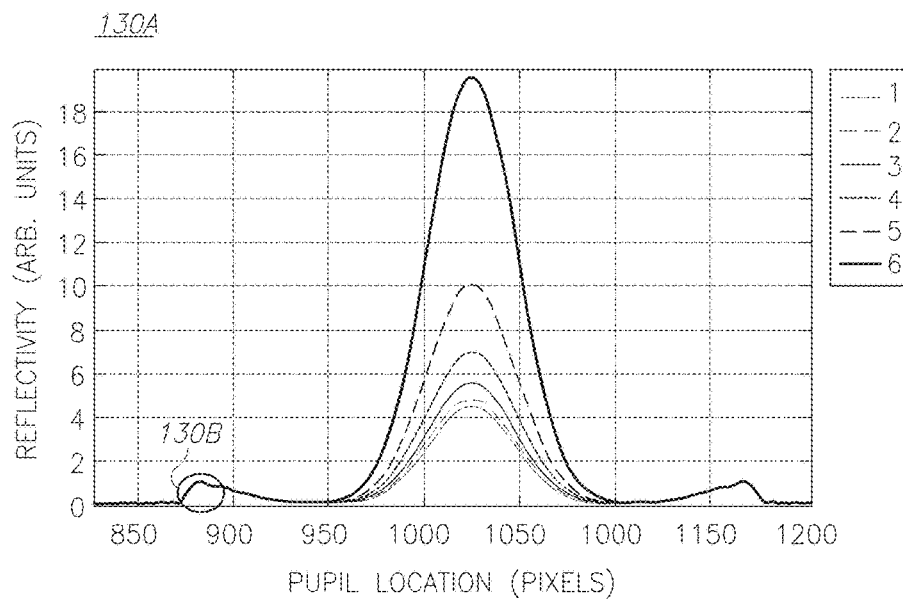
FIGS. 3A-3D present a simulation that supports the proposed model and method according to some embodiments of the invention.
Figure 3B:
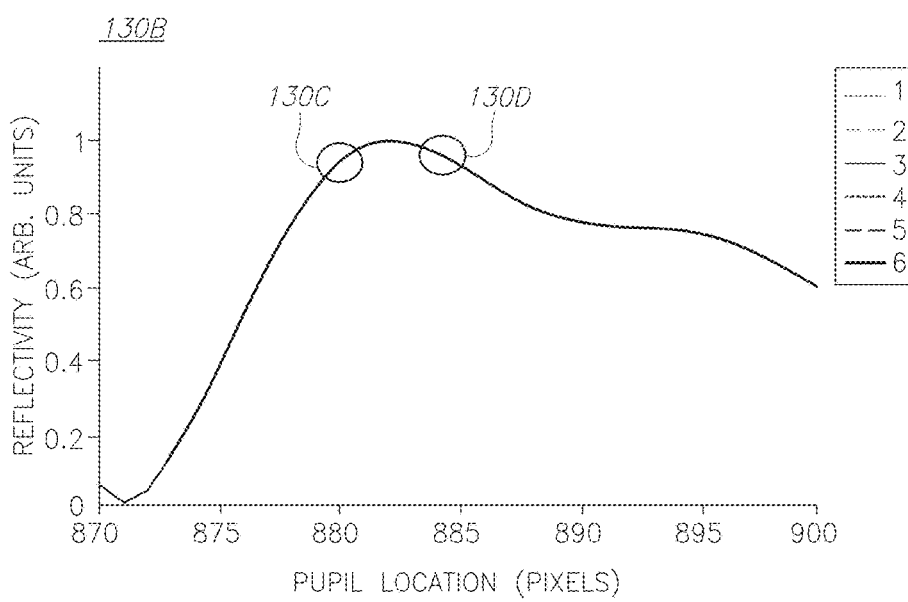
Figure 3C:
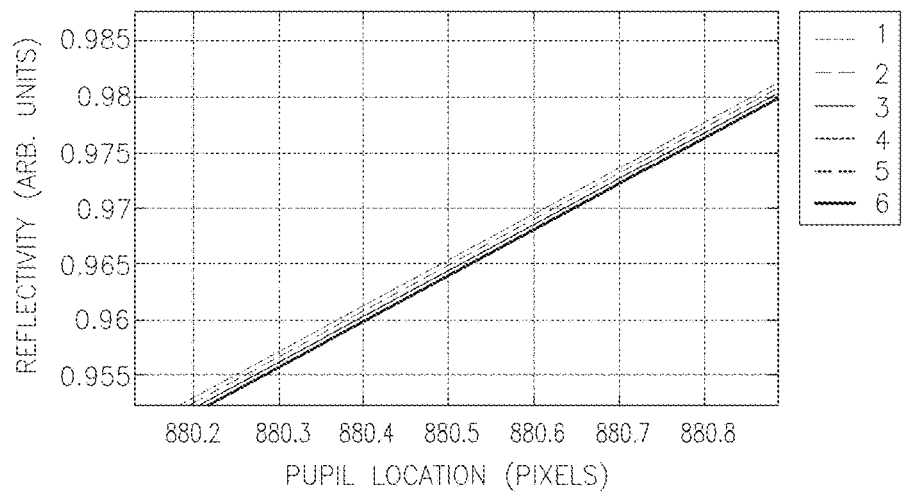
Figure 3D:
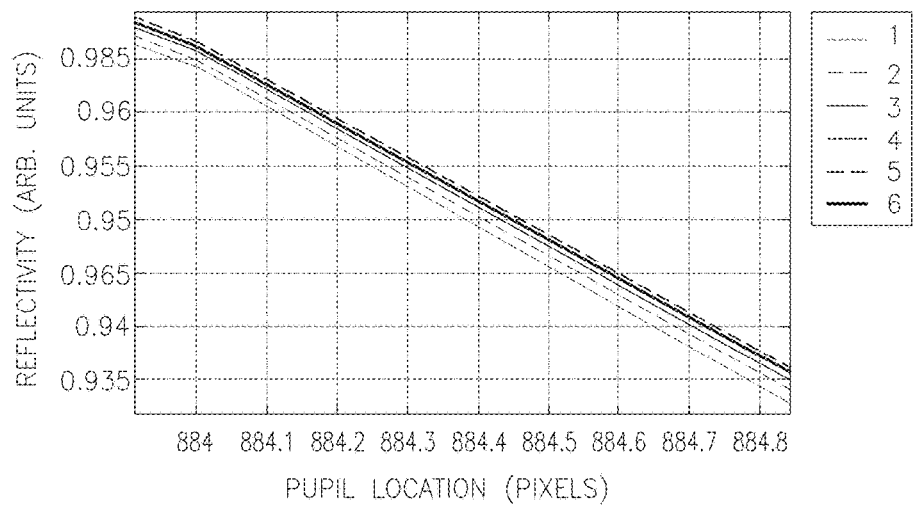

FIG. 2D presents in diagram 128 the overlay thus calculated (denoted as peak movement OVL) as a function of the reported overlay, derived by standard methods. Clearly the correlation is strong, thus the measured peak locations provide a good estimation of the overlay.

FIGS. 3A-3D present a simulation that supports the proposed model and method according to some embodiments of the invention. The curves correspond to six overlay values, increasing from 1 to 6, for simulated grating over grating targets. Simulated reflection intensity values are shown at three scales—diagram 130A (FIG. 3A) shows the reflectivity across the NA (numerical aperture; the central peak correspond to the zeroth order spot and the small lateral peaks correspond to the ±first orders shown schematically as spots 70 in FIG. 1, note the similar magnitude and opposite signs of the ±1 orders); diagram 130B (FIG. 3B) is a magnification of the minus first order spot; and diagrams 130C, 130D (FIGS. 3C, 3D respectively) are further magnifications of sections from the intensity curve at either sides of the peak of the minus first order spot. The four diagrams use the same pixel location scale. Diagrams 130C, 130D illustrate the functional dependency of the peak location on the overlay, or offset, as was expressed above in K=f(OFFSET, Order), i.e., that the offset of the spots corresponds to the changes in the overlay represented by the six curves. The difference between the lines is caused by a combination of lateral shift and vertical stretching. This shift can be used for example to extract the OVL as described above.

Figure 4:
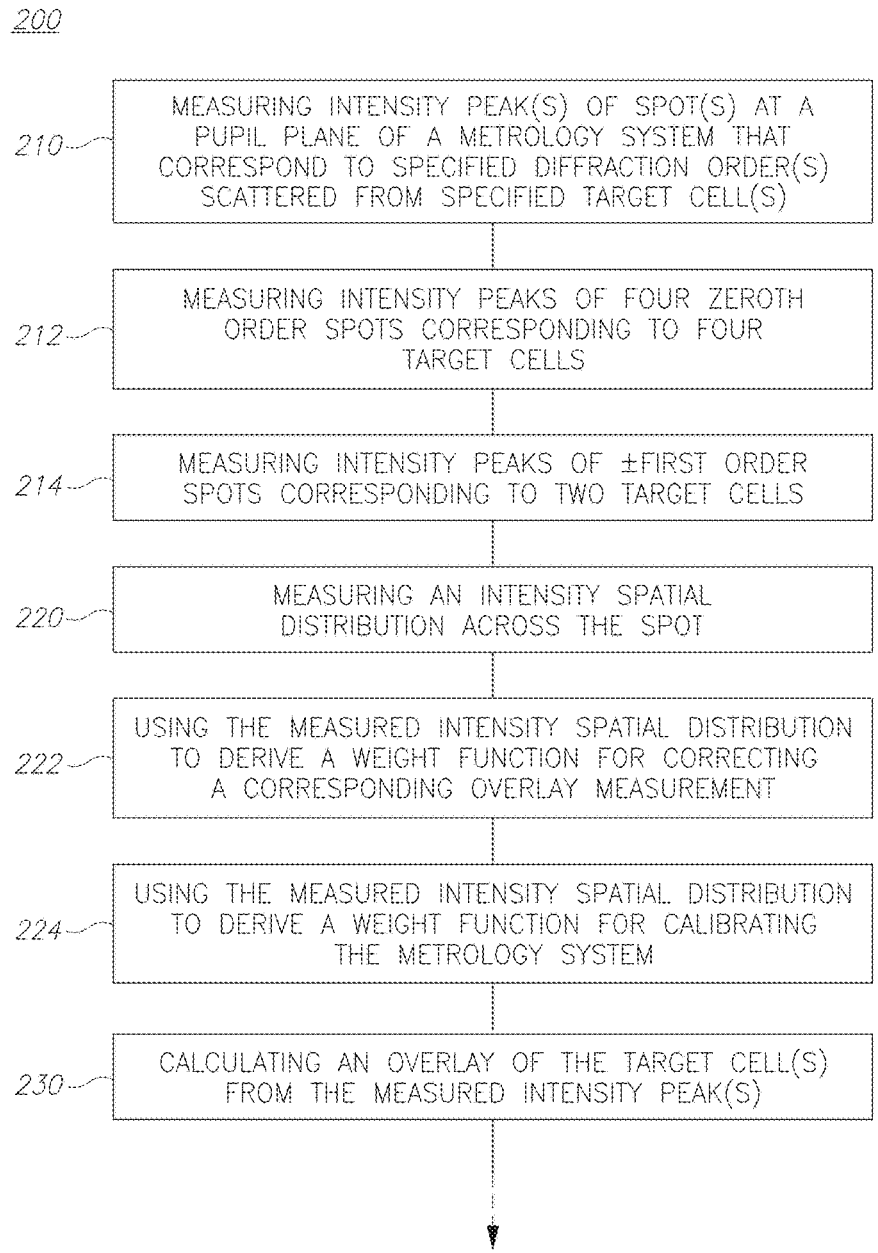
FIG. 4 is a high level flowchart illustrating a method, according to some embodiments of the invention.

In certain embodiments, any parameters of the intensity spatial distribution may be used to calculate the overlays, e.g., even if peaks are not discernable or if there are multiple peaks in the distribution, FIG. 4 is a high level flowchart illustrating a method 200, according to some embodiments of the invention. Respective stages of method 200 may at least partially be performed by a computer processor and or an overlay module integrated in a metrology tool.

Method 200 comprises measuring an intensity peak of at least one spot at a pupil plane of a metrology system that corresponds to a specified diffraction order scattered from a specified target cell (stage 210) and calculating an overlay of the target cell from the at least one measured intensity peak (stage 230). For example, measuring 210 may comprise measuring intensity peaks of four zeroth order spots corresponding to four target cells (stage 212) and calculating 230 may be carried out with respect thereto. In another example, measuring 210 may comprise measuring intensity peaks of ±first order spots corresponding to two target cells (stage 214) and calculating 230 may be carried out with respect thereto.

Method 200 may further comprise measuring an intensity spatial distribution across the spot (stage 220) and deriving the intensity peak therefrom (stage 240). In certain embodiments, the measured intensity spatial distribution may be used to derive a weight function for correcting a corresponding overlay measurement (stage 222). In certain embodiments, the measured intensity spatial distribution may be used to derive a weight function for calibrating the metrology system (stage 224).

Advantageously, disclosed models, methods and modules provide a new way of getting overlay information from the same measurements used in conventional SCOL tools. This new information can be used for several applications, such as in alternative methods for overlay calculation, possibly using a smaller number of target cells and\or of diffraction orders than current methods. A comparison of the disclosed algorithms to the standard ones may be used, e.g., (i) to derive accuracy and\or performance scores for metrology recipes, (ii) to calibrate the pupil by optimizing the matching between the overlay measurement methods, for example, by determining the calibrated pupil as the one that gives the best correlation between the overlay and the peak locations and/or (iii) as a flag for indicating imperfections in targets and/or the optical system.

In certain embodiments, the proposed methods may be used to calculate the overlay using only a single cell, e.g., to achieve faster measurements with some performance penalty (e.g., higher TMU-total measurement uncertainty or lower accuracy), and may be combined with the standard OVL algorithm to provide sampling which optimizes throughput, TMU, accuracy and real estate.

Method 200 may hence further comprise comparing the calculated overlay with a standard overlay measurement (stage 250) to evaluate a given metrology recipe (stage 252) and/or to calibrate the pupil by optimizing a matching between the calculated overlay and the standard overlay measurement (stage 254) and/or to provide an indication of exceptional targets or measurement conditions (stage 256). In certain embodiments, method 200 may comprise carrying out the measuring and the calculating with respect to a single target cell (stage 260).

An overlay metrology module (associated with the metrology tool or system) may be configured to measure an intensity peak of at least one spot at a pupil plane of a metrology system that corresponds to at least one specified diffraction order scattered from at least one specified target cell, and calculate at least one overlay of the at least one target cell from the at least one measured intensity peak. The metrology module may be configured to implement any of the stages of method 200 and/or any aspect of model 100.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method comprising:
   measuring, with a metrology tool, at a pupil plane of an optical system of the metrology tool a reflection signal from a plurality of zeroth-order spots corresponding with a plurality of zeroth order intensity peaks scattered from a plurality of target cells;
   fitting, with one or more processors communicatively coupled to the optical system of the metrology tool, a function to approximate a spatial distribution of an intensity across the plurality of zeroth-order spots measured at the pupil plane;
   determining, with the one or more processors communicatively coupled to the optical system of the metrology tool, a plurality of intensity peak positions of the function;
   calculating a weight function based on the approximated spatial distribution of the intensity across the plurality of zeroth-order spots measured at the pupil plane; and
   calibrating the metrology tool based on the calculated weight function; and
   calculating, with the one or more processors communicatively coupled to the optical system of the metrology tool, an overlay of a target based on a portion of one or more measurements of the reflection signal from the plurality of zeroth-order spots corresponding with the plurality of spots.

2. The method of claim 1, wherein:
   the measuring further comprises measuring intensity peaks of ±first order spots corresponding to two target cells; and
   the calculating of the overlay of the target is carried out with respect to the measured intensity peaks of the ±first order spots corresponding to the two target cells.

3. The method of claim 1, further comprising comparing the calculated overlay with a standard overlay measurement to evaluate a given metrology recipe.

4. The method of claim 1, further comprising comparing the calculated overlay with a standard overlay measurement to calibrate the pupil by optimizing a matching between the calculated overlay and the standard overlay measurement.

5. The method of claim 1, further comprising comparing the calculated overlay with a standard overlay measurement to provide an indication of exceptional targets or measurement conditions.

6. The method of claim 1, wherein the metrology tool comprises an angled resolved scatterometry overlay metrology tool.

7. The method of claim 1, wherein the plurality of target cells comprises four target cells.

8. An overlay metrology system comprising:
   an optical system configured to measure at a pupil plane of the overlay metrology system a reflection signal from a plurality of zeroth-order spots corresponding with a plurality of zeroth order intensity peaks scattered from a plurality of target cells; and one or more processors communicatively coupled to the optical system and configured to:

fit a function to approximate a spatial distribution of an intensity across the plurality of zeroth-order spots measured at the pupil plane;

determine a plurality of intensity peak positions of the function;

calculate a weight function based on the approximated spatial distribution of the intensity across the plurality of zeroth-order spots measured at the pupil plane;

calibrate the metrology system based on the calculated weight function; and calculate an overlay of a target based on a portion of one or more measurements of the reflection signal from the plurality of zeroth-order spots corresponding with the plurality of zeroth order intensity peaks.

9. The system of claim 8, wherein the one or more processors are further configured to compare the calculated overlay with a standard overlay measurement to evaluate a given metrology recipe.

10. The system of claim 8, wherein the one or more processors are further configured to compare the calculated overlay with a standard overlay measurement to calibrate the pupil by optimizing a matching between the calculated overlay and the standard overlay measurement.

11. The system of claim 8, wherein the one or more processors are further configured to compare the calculated overlay with a standard overlay measurement to provide an indication of exceptional targets or measurement conditions.

12. The system of claim 8, wherein the overlay metrology system comprises an angled resolved scatterometry overlay system.

13. The system of claim 8, wherein the plurality of target cells comprises four target cells.

* * * * *